United States Patent [19]

Hyatt

[11] Patent Number: 5,869,704
[45] Date of Patent: Feb. 9, 1999

[54] WATER-DISPERSIBLE OR WATER-SOLUBLE D-TOCOTRIENOL COMPOUNDS AND METHODS FOR MAKING THEREFOR

[75] Inventor: John A. Hyatt, Kingsport, Tenn.

[73] Assignee: Eastman Chemical Company, Kingsport, Tenn.

[21] Appl. No.: 138,785

[22] Filed: Aug. 24, 1998

[51] Int. Cl.$^6$ ................................................. C07D 311/72
[52] U.S. Cl. ........................................ 549/410; 549/412
[58] Field of Search ...................... 549/410, 412

[56] References Cited

U.S. PATENT DOCUMENTS

| | | | |
|---|---|---|---|
| 2,680,749 | 6/1954 | Cawley et al. | |
| 3,102,078 | 8/1963 | Robeson. | |
| 5,348,974 | 9/1994 | Wright et al. | 514/456 |
| 5,393,776 | 2/1995 | Pearce | 514/486 |
| 5,430,021 | 7/1995 | Rudnic et al. | 514/14 |
| 5,554,647 | 9/1996 | Perricone | 514/474 |
| 5,591,772 | 1/1997 | Lane et al. | 514/458 |
| 5,670,668 | 9/1997 | Hyatt | 549/410 |

FOREIGN PATENT DOCUMENTS

| | | |
|---|---|---|
| 0571928 A1 | 12/1993 | European Pat. Off. . |
| 0669132 A | 8/1995 | European Pat. Off. . |
| 61-060619 A | 3/1986 | Japan . |
| 63-120686 A | 5/1988 | Japan . |
| 9507722 B | 7/1995 | Rep. of Korea . |
| 95/31217 | 11/1995 | WIPO . |

OTHER PUBLICATIONS

Goh et al., Tocotrienols from Palm Oil; Electron Spin Resonance Spectra of Tocotrienoxyl Radicals, J. Am. Oil Chem. Soc., 67(4), 250–4, 1990 (abstract).

*Primary Examiner*—Fiona T. Powers
*Attorney, Agent, or Firm*—Michael J. Blake; Harry J. Gwinnell

[57] ABSTRACT

The invention relates to a water-dispersible or water-soluble compound having the structure I

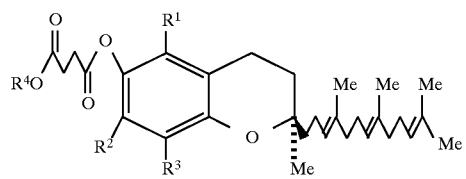

wherein, $R^1, R^2$, and $R^3$ are, independently, hydrogen or methyl, and $R^4$ is —$(CH_2CH_2O)_nCH_2CH_2OH$, wherein n is from 10 to 100, wherein compound I is the substantially pure D-enantiomer. The invention further relates to a water-dispersible or water-soluble compound having the structure II

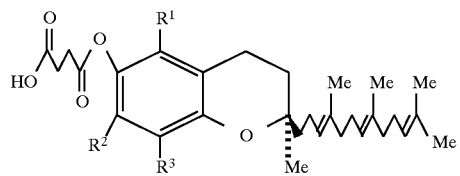

wherein, $R^1$, $R^2$, and $R^3$ are, independently, hydrogen or methyl, or the salt thereof, wherein compound II is the substantially pure D-enantiomer. The invention further relates to methods for making the tocotrienol compounds of the present invention.

15 Claims, No Drawings

WATER-DISPERSIBLE OR WATER-SOLUBLE D-TOCOTRIENOL COMPOUNDS AND METHODS FOR MAKING THEREFOR

FIELD OF THE INVENTION

The present invention relates to water-dispersible or water-soluble D-tocotrienol compounds and methods for making therefor.

BACKGROUND OF THE INVENTION

D-Tocotrienols possess a number of properties that can aid in the treatment of various human diseases. In particular, D-gamma-tocotrienol is reported to have several beneficial physiological effects in humans. D-gamma-tocotrienol is a substance that occurs naturally at low levels in many plant tissues (see Bauernfield in "Vitamin E, A Comprehensive Treatise," ed. L. Machlin, Marcel Dekker, New York, 1980, pp. 99–167). D-gamma-tocotrienol possesses antitumor activity (see Kato et al., *J. Jpn. Oil Chemists Soc.* 34, pp. 375, 1985; Komiyama et al., *Chem. Pharm, Bull.* 37, pp. 1369, 1989), antihypercholesterolemic activity (see Qureshi et al., *Am. J Clin. Nutr.* 53, pp. 1021S, 1991; Watkins et al., *Lipids* 28, pp. 1113, 1993; Tan et al., *Am. J Clin. Nutr.* 53, pp. 1027S, 1991; Parker et al., *J. Biol. Chem.* 268, pp. 11230, 1993; European Patent Application No. 90119040.5, and U.S. Pat. No. 5,217,992), and antioxidant activity (see Yamaoka et al., *J. Am. Oil Chemists Soc.* 68, pp. 114, 1991). Thus, D-tocotrienols are useful as pharmaceutical materials and as nutritional supplements.

One problem associated with naturally-occurring D-tocotrienols is their poor solubility or insolubility in water. The poor solubility in water limits the ability of D-tocotrienols to be admixed with other components in an aqueous media. The poor solubility of tocotrienols also limits their usefulness for parental injection. The prior art does not disclose a method for overcoming this problem. Thus, one object of the present invention is to increase the water-solubility of D-tocotrienols.

The prior art discloses the preparation of water-soluble tocopherol compounds. U.S. Pat. No. 2,680,749 to Cawley et al.; U.S. Pat. No. 3,102,078 to Robeson et al.; U.S. Pat. No. 5,430,021 to Rudnic et al.; and International Publication No. WO 95/31217 to Sonne disclose polyethoxylated succinate esters of tocopherol. These references, however, do not disclose the preparation of polyethoxylated succinate esters of tocotrienols, particularly of D-tocotrienols.

The prior art also discloses the synthesis of succinate esters of tocotrienols (see U.S. Pat. No. 5,348,974 to Wright et al.; U.S. Pat. No. 5,554,647 to Perricone; European Patent Publication No. 0571928 A1 to Pearce; European Patent Publication No. 0669132 A1 to Liqui; Japanese Patent Application No. 61060619; and Goh et al., J. Am. Oil Chem. Soc., 67, pp 250–254, 1990). These references, however, do not disclose polyethoxylating the tocotrienol succinate esters. Additionally, these references only disclose the preparation of succinate esters of racemic mixtures of tocotrienols and not the D-enantiomer.

Korean Patent Application No. 9507722 B to Ha et al. discloses a composition for skin detergent possessing protective properties against UV light. The composition contains polyethoxylated tocopherols or tocotrienols and its ester thereof. These compounds are not a feature of the present invention. Moreover, there is no disclosure in Ha et al. for preparing the succinate ester of D-tocotrienols.

In light of the above, it would be very desirable to produce water-dispersible D-tocotrienol compounds that can be used as pharmaceutical materials and nutritional supplements.

SUMMARY OF THE INVENTION

In accordance with the purpose(s) of this invention, as embodied and broadly described herein, this invention, in one aspect, relates to a water-dispersible or water-soluble compound having the structure I

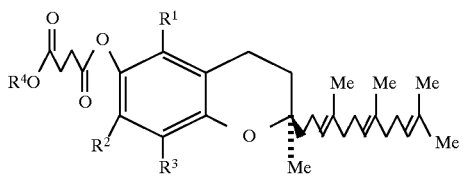

wherein, $R^1$, $R^2$, and $R^3$ are, independently, hydrogen or methyl, and $R^4$ is —$(CH_2CH_2O)_nCH_2CH_2OH$, wherein n is from 10 to 100, wherein compound I is the substantially pure D-enantiomer.

The invention further relates to a water-dispersible or water-soluble compound having the structure II

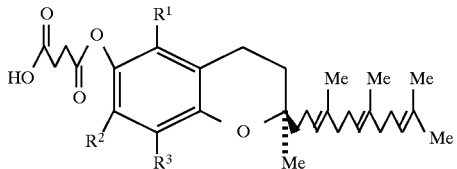

wherein, $R^1$, $R^2$, and $R^3$ are, independently, hydrogen or methyl, or the salt thereof, wherein compound II is the substantially pure D-enantiomer.

The invention further relates to a method for preparing the compound having the structure I, comprising reacting a compound having the structure II

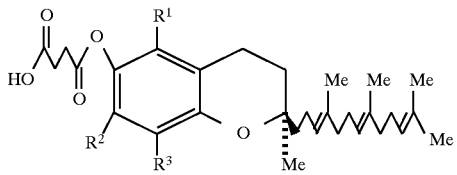

with poly(ethylene glycol)

wherein, $R^1$, $R^2$, and $R^3$ are, independently, hydrogen or methyl, wherein compound II is the substantially pure D-enantiomer.

The invention further relates to a method for making the compound having the structure II, comprising reacting a compound having the structure III

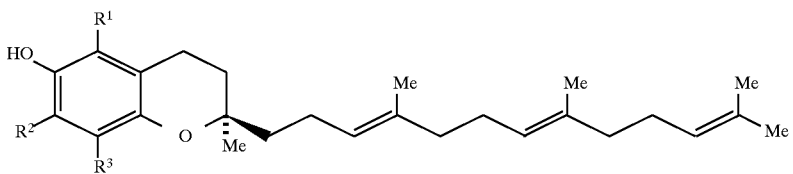

with an acylating agent comprising succinic anhydride or succinic acid wherein, $R^1$, $R^2$, and $R^3$ are, independently, hydrogen or methyl, wherein compound III is the substantially pure D-enantiomer.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included therein.

Before the present compositions of matter and methods are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

The singular forms "a," "an" and "the" include plural referents unless the context clearly dictates otherwise.

"Optional" or "optionally" means that the subsequently described event or circumstance may or may not occur, and that the description includes instances where said event or circumstance occurs and instances where it does not.

Tocotrienols or compounds of the present invention refer to compounds I and II.

The phrase "water-dispersible" is defined as the ability of the tocotrienols of the present invention to form an emulsion upon addition to water. The term "water-soluble" is defined as the ability of the tocotrienols of the present invention to dissolve in water. Naturally-occurring D-tocotrienols are water-insoluble. The tocotrienols of the present invention are not water-insoluble. The tocotrienols of the present invention thus do not form an insoluble or immiscible layer as would naturally-occurring tocotrienols of the prior art. The tocotrienols of the present invention disperse to form an emulsion in water or are soluble in water. In one embodiment, an aqueous solution comprises from 0.1 to 5% by weight of a tocotrienol compound of the present invention and from 95 to 99.9% by weight water, wherein the tocotrienol compound is completely soluble in the water.

The compounds having the structure I are more soluble in water than the compounds having the structure II.

The phrase "substantially pure" as used herein refers to the enantiomeric purity of the D-enantiomer of the compound compared to the L-enantiomer, wherein the D-enantiomer is greater than 50% enantiomeric purity in a D/L mixture, preferably with a higher enantiomeric purity, more preferably from 55 to 100%, more preferably from 75 to 100%, more preferably from 85 to 100%, more preferably from 95 to 100%, and even more preferably 100% D-enantiomer. For example, when compound A is a mixture of 80% of the D-enantiomer and 20% of the L-enantiomer, then the enantiomeric purity of the D-enantiomer is 80% and the enantiomeric purity of the L-enantiomer is 20%.

The tocotrienol compounds of the present invention are also soluble in organic solvents. In one embodiment, an organic solution comprises from 0.1 to 20% by weight of a tocotrienol compound of the present invention and from 80 to 99.9% by weight of the organic solvent, wherein the tocotrienol compound is completely soluble in the organic solvent. Examples of organic solvents that can solubilize the tocotrienol compounds include, but are not limited to, ethyl acetate and toluene.

The hydrogen atoms on the single and double bonds in structures I, II, and III have been omitted for clarity. Unless stated otherwise, it is understood that the single bonds are methylene linkages (—$CH_2$—) and the double bonds have one hydrogen atom attached to the double bond. The abbreviation "Me" represent a methyl group.

In accordance with the purpose(s) of this invention, as embodied and broadly described herein, this invention, in one aspect, relates to a water-dispersible or water-soluble compound having the structure II

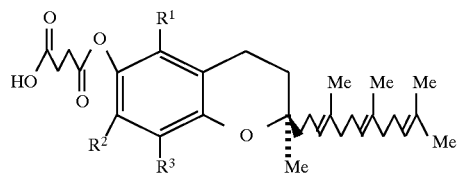

wherein, $R^1$, $R^2$, and $R^3$ are, independently, hydrogen or methyl, or the salt thereof, wherein compound II is the substantially pure D-enantiomer.

In one embodiment, the salt of compound II can be an alkali metal salt. Examples of alkali metal salts of compound II include, but are not limited to, the sodium or potassium salts.

In one embodiment, the compound having the structure II has an enantiomeric purity for the D-enantiomer of from 55 to 100%, preferably from 75 to 100%, more preferably from 85 to 100%, more preferably from 95 to 100%, and even more preferably 100%. In one embodiment, when the compound has the structure II, $R^1$ is hydrogen, and $R^2$ and $R^3$ are methyl (D-γ-tocotrienyl hemisuccinate). In one embodiment, when the compound has the structure II, $R^1$, $R^2$ and $R^3$ are methyl (D-α-tocotrienyl hemisuccinate). In one embodiment, when the compound has the structure II, $R^2$ is hydrogen, and $R^1$ and $R^3$ are methyl (D-β-tocotrienyl hemisuccinate). In one embodiment, when the compound has the structure II, $R^1$ and $R^2$ are hydrogen, and $R^3$ is methyl (D-δ-tocotrienyl hemisuccinate).

The invention further relates to a method for making a compound having the structure II, comprising reacting a compound having the structure III

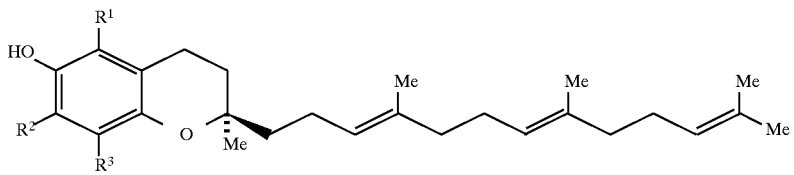

with an acylating agent comprising succinic anhydride or succinic acid
wherein,
$R^1$, $R^2$, and $R^3$ are, independently, hydrogen or methyl,
wherein compound III is the substantially pure D-enantiomer.

The process typically involves admixing (1) a D-enantiomer of a tocotrienol, (2) succinic anhydride or succinic acid, and (3) a base. In one embodiment, succinic anhydride is the acylating agent. In one embodiment, the base comprises potassium acetate, sodium acetate, pyridine, quinoline, sodium carbonate, or sodium bicarbonate. In one embodiment, the process is conducted under an inert atmosphere at an elevated temperature. In one embodiment, the inert atmosphere is argon and the temperature is from 100° to 110° C. The composition containing the succinate ester II can be washed with water, dried, and the solvent removed in order to provide the purified succinate ester. The succinate esters having the structure II can be further purified using techniques known in the art. In one embodiment, the compound having the structure II is produced from compound II, wherein the enantiomeric purity of the D-enantiomer of compound III is from 55 to 100%, preferably from 75 to 100%, more preferably from 85 to 100%, more preferably from 95 to 100%, and even more preferably 100%.

The invention further relates to a water-dispersible or water-soluble compound having the structure I

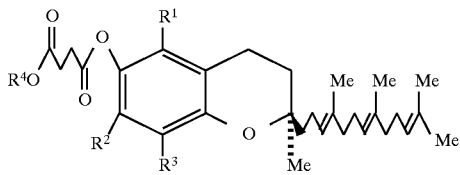

wherein,
$R^1$, $R^2$, and $R^3$ are, independently, hydrogen or methyl, and
$R^4$ is —$(CH_2CH_2O)_nCH_2CH_2OH$, wherein n is from 10 to 100,
wherein compound I is the substantially pure D-enantiomer.

n is preferably from 10 to 90, more preferably from 18 to 34, more preferably from 20 to 25, and even more preferably about 23.

In one embodiment, the compound having the structure I has an enantiomeric purity for the D-enantiomer of from 55 to 100%, preferably from 75 to 100%, more preferably from 85 to 100%, more preferably from 95 to 100%, and even more preferably 100%. In one embodiment, when the compound has the structure I, $R^1$ is hydrogen, and $R^2$ and $R^3$ are methyl (D-γ-tocotrienyl poly(ethylene glycol) succinate). In one embodiment, when the compound has the structure I, $R^1$, $R^2$ and $R^3$ are methyl (D-α-tocotrienyl poly(ethylene glycol) succinate). In one embodiment, when the compound has the structure I, $R^2$ is hydrogen, and $R^1$ and $R^3$ are methyl (D-β-tocotrienyl poly(ethylene glycol) succinate). In one embodiment, when the compound has the structure I, $R^1$ and $R^2$ are hydrogen, and $R^3$ is methyl (D-δ-tocotrienyl poly(ethylene glycol) succinate).

The invention further relates to a method for preparing the compounds having the structure I, comprising reacting a compound having the structure II

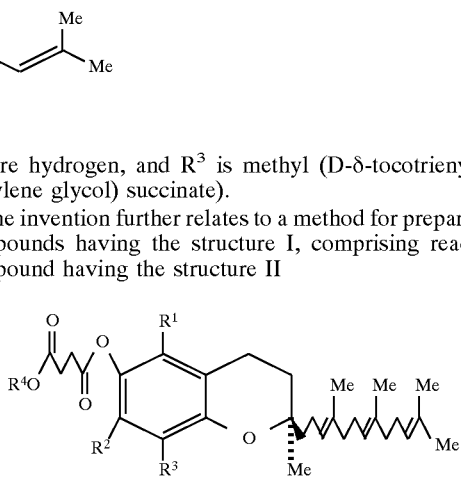

with poly(ethylene glycol)
wherein,
$R^1$, $R^2$, and $R^3$ are, independently, hydrogen or methyl,
wherein compound II is the substantially pure D-enantiomer.

The process typically involves admixing the succinate ester compound II and poly(ethylene glycol) in an organic solvent. In one embodiment, the polyethylene glycol) has a molecular weight of from 400 to 4,262, preferably from 400 to 4,000, more preferably from 800 to 1,200, more preferably from 902 to 1,162, and even more preferably about 1,000. In one embodiment, the composition is refluxed, and water is removed using techniques known in the art. Removal of the solvent affords a composition composed of compound III and unreacted poly(ethylene glycol) (PEG). Compound I can be separated from the composition containing the unreacted PEG using techniques known in the art. In one embodiment, the compound having the structure I is produced from compound II, wherein the enantiomeric purity of the D-enantiomer of compound II is from 55 to 100%, preferably from 75 to 100%, more preferably from 85 to 100%, more preferably from 95 to 100%, and even more preferably 100%.

An esterification catalyst can also be added to the admixture comprising the succinate ester compound II and poly(ethylene glycol) in order to facilitate the esterification of the succinate ester II. In one embodiment, the esterification catalyst comprises p-toluenesulfonic acid, methanesulfonic acid, sulfuric acid, camphor sulfonic acid, or a polymeric or resin acid. Examples of polymeric or resin acids include, but are not limited to, AMBERLYST® or NAFION® resins. In one embodiment, the esterification catalyst comprises p-toluenesulfonic acid.

The water-dispersible or water-soluble tocotrienols of the present invention provide all of the health or pharmaceutical benefits of naturally-occurring, unesterified tocotrienols with the added benefit that the tocotrienols of the present invention possess greater solubility in water when compared to naturally-occurring tocotrienols. Moreover, compounds I and II of the present invention are in substantially pure form. As described above, tocotrienols can be used in the treatment or prevention of a number of human or animal diseases. The tocotrienol compounds of the present invention facilitate the administration of the tocotrienol to a subject. The tocotrienol compounds of the present invention can be used to treat or prevent the same diseases known to be treatable with naturally-occurring, unesterified tocotrienols with the advantage that the tocotrienols of the present invention are easier to deliver due to their increased water-solubility. Parameters for methods of treatment or prevention utilizing the inventive compounds including, but not limited to, dosages, modes of administration, treatment regimens, carriers, diluents, and other inert ingredients, would be obvious to one of ordinary skill in the art based on the disclosure herein and based on the same or similar methods of treatment or prevention used for naturally-occurring, unesterified tocotrienols.

EXAMPLES

The following examples are put forth so as to provide those of ordinary skill in the art with a complete disclosure and description of how the compositions of matter and methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature and pressure is at or near atmospheric.

Example 1

Preparation of D-γ-tocotrienyl hemisuccinate (compound II, $R^1$ is hydrogen, and $R^2$ and $R^3$ are methyl)

A mixture of 10.3 g of D-γ-tocotrienol (0.025 mol), 4.0 g of powdered succinic anhydride (0.04 mol), and 0.25 g of potassium acetate were stirred under an argon atmosphere at a temperature of from 100° to 110° C. for three hours, at which time thin-layer chromatographic analysis indicated the consumption of the tocotrienol and formation of a singular polar product. The mixture was allowed to cool, diluted with 100 mL of ethyl acetate, and washed with water (4×100 mL). The organic phase was dried over anhydrous magnesium sulfate, filtered, and stripped of volatiles to provide 13.1 g of product as a pale, yellow, viscous syrup. Proton NMR analysis (CDCl$_3$, 300 MHz, ppm): 1.29 (s, 3H); 1.60 (br s, 9H); 1.67 (br s, 3H); 2.04 (s, 3H); 2.12 (s, 3H); 1.4–2.2 (broad m, 14H); 2.71 (br t, 2H); 2.81 (m, 2H); 2.90 (m, 2H); 5.12 (br m, 3H); 6.57 (s, 1H). Elemental analysis: Calculated, C, 75.3%; H, 9.08%. Found, C, 75.7%; H, 9.34.

Example 2

Preparation of D-γ-tocotrienyl poly(ethylene glycol) succinate (compound I, $R^1$ is hydrogen, and $R^2$ and $R^3$ are methyl)

A solution of 12.8 g of D-γ-tocotrienyl hemisuccinate in 250 mL of toluene containing 0.25 grams of p-toulenesulfonic acid was treated with 75 g of poly (ethylene glycol) having a molecular weight of 1,000 (0.75 mol). The reaction mixture was refluxed under Dean-Stark water removal for 10 hours, treated with 0.5 g of sodium bicarbonate, and the toluene was removed under vacuum. The desired product can be separated from residual, unreacted poly(ethylene glycol) by chromatography or extraction. After purification, 16 g of a yellow syrup was isolated, which solidified upon standing. The material can be recrystallized from cold ethanol and has a melting point of from 35° to 42° C. The product was soluble in water and organic solvents. The product also exhibits surfactant properties. Proton NMR spectrum (CDCl$_3$ solution, 300 MHz, ppm): 1.12 (s, 3H); 1.58 (br s, 9H); 1.69 (s, 3H); 2.00 (s, 3H); 2.14 (s, 3H); 1.4–2.2 (br m, 14H); 2.68 (br t, 2H); 2.75 (m, 2H); 2.87 (m, 2H); 3.7 (br s, 96H); 4.22 (m, 2H); 5.10 (brm, 3H); 6.58 (s, 1H).

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A water-dispersible or water-soluble compound having the structure I

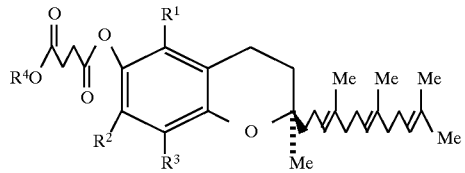

wherein, $R^1$, $R^2$, and $R^3$ are, independently, hydrogen or methyl, and $R^4$ is —(CH$_2$CH$_2$O)$_n$CH$_2$CH$_2$OH, wherein n is from 10 to 100, wherein compound I is the substantially pure D-enantiomer.

2. The compound of claim 1, wherein $R^1$ is hydrogen, and $R^2$ and $R^3$ are methyl.

3. The compound of claim 1, wherein $R^1$, $R^2$ and $R^3$ are methyl.

4. The compound of claim 1, wherein $R^2$ is hydrogen, and $R^1$ and $R^3$ are methyl.

5. The compound of claim 1, wherein $R^1$ and $R^2$ are hydrogen, and $R^3$ is methyl.

6. The compound of claim 1, wherein the purity of the D-enantiomer is from 85 to 100%.

7. The compound of claim 1, wherein the purity of the D-enantiomer is from 95 to 100%.

8. The compound of claim 1, wherein the purity of the D-enantiomer is 100%.

9. A method for preparing the compound of claim 1, comprising reacting a compound having the structure II

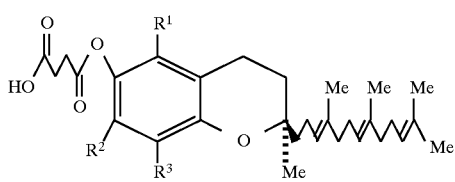

with poly(ethylene glycol)

wherein, $R^1$, $R^2$, and $R^3$ are, independently, hydrogen or methyl, wherein compound II is the substantially pure D-enantiomer.

10. The method of claim 9, wherein the poly(ethylene glycol) has a molecular weight of from 400 to 4,000.

11. The method of claim 9, wherein the poly(ethylene glycol) has a molecular weight of from 800 to 1,200.

12. The method of claim 9, wherein the poly(ethylene glycol) has a molecular weight of about 1,000.

13. The method of claim 9, further comprising an esterification catalyst.

14. The method of claim 13, wherein the esterification catalyst comprises p-toluenesulfonic acid, methanesulfonic acid, sulfuric acid, camphorsulfonic acid, or a polymeric or resin acid.

15. The method of claim 13, wherein the esterification catalyst comprises p-toluenesulfonic acid.

* * * * *